United States Patent [19]

Hruby et al.

[11] Patent Number: 4,866,038

[45] Date of Patent: Sep. 12, 1989

[54] METHOD OF STIMULATING INTEGUMENTAL MELANOCYTES BY TOPICAL APPLICATION OF ANALOGS OF ALPHA-MSH

[75] Inventors: Victor J. Hruby; Mac E. Hadley; Robert Dorr; Norman Levine, all of Tucson, Ariz.; Elizabeth Sugg, High Bridge; Wayne L. Cody, Ringoes, both of N.J.

[73] Assignee: University Patents, Inc., Westport, Conn.

[21] Appl. No.: 224,187

[22] Filed: Jul. 22, 1988

Related U.S. Application Data

[63] Continuation of Ser. No. 825,162, Feb. 3, 1986, abandoned.

[51] Int. Cl.$^4$ .............................................. A61K 37/24
[52] U.S. Cl. ....................................... 514/14; 514/805
[58] Field of Search ................................. 514/14, 805

[56] References Cited

U.S. PATENT DOCUMENTS

| | | | |
|---|---|---|---|
| 3,803,309 | 4/1974 | Antoine et al. ...................... | 514/14 |
| 4,457,864 | 7/1984 | Hruby ................................. | 530/312 |
| 4,485,039 | 11/1984 | Hruby ................................. | 530/312 |

OTHER PUBLICATIONS

Eberle et al., *Helvetica Chemica Acta*, 58(6), 1528–1535 (1975).

Cody et al., *Journal of Chromatography*, 314, 313–321 (1984).

*Primary Examiner*—Delbert R. Phillips
*Assistant Examiner*—F. T. Moezie
*Attorney, Agent, or Firm*—George M. Yahwak

[57] ABSTRACT

A method for stimulating integumental melanocytes by the topical application of alpha-MSH analogs, and compositions comprising said analogs for use in the method are described.

21 Claims, No Drawings

METHOD OF STIMULATING INTEGUMENTAL MELANOCYTES BY TOPICAL APPLICATION OF ANALOGS OF ALPHA-MSH

Partial funding for the research leading up to the making of the invention described herein was received from the U.S. Government. Accordingly, the Federal Government of the United States retains certain rights to the invention described herein under Chapter 38 of Title 35 of the U.S. Code.

This application is a continuation of application Ser. No. 825,162 filed Feb. 3, 1986, now abandoned.

The present invention concerns methods of stimulating integumental melanocytes in vertebrates by the topical application of certain alpha-MSH analogs, and compositions useful in the novel method.

In vertebrates, the color of their skin, fur, and feathers is determined by the number and distribution of certain color-bearing cells, e.g. melanocytes, the number and distribution of which melanocytes is under genetic control. Melanocytes in mammals are localized at the basal layer of the epidermis, at the dermal-epidermal junction, and within hair follicles. Synthesis of pigment (melanin) within these melanocytes is controlled by the activity of an enzyme, tyrosinase, which is localized in an intracellular organelle, the premelanosome. Upon activation of tyrosinase, either eumelanin (brown-black) or phaeomelanin (yellow-red) pigment is deposited within the organelle; after complete melanization, the premelanosome is known as a melanosome, more specifically either an eumelanosome or a phaeomelanosome depending upon color [see Fitzpatrick, T. B., Y. Hori, K. Toda, M. Seiji, Jap. J. Derm. 79:278(1969)]. Melanosomes are delivered to surrounding keratinocytes of the skin or to cells within the shaft of the growing hair by the process known as cytocrine secretion.

Although melanin synthesis and pelage patterns are expressed genetically, follicular melanogenesis and pelage color changes in some mammals may be hormonally controlled by alpha-melanotropin (also known as alphamelanocyte stimulating hormone, or alpha-MSH), a tridecapeptide of the formula:

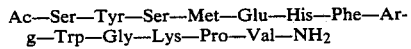

Ac—Ser—Tyr—Ser—Met—Glu—His—Phe—Arg—Trp—Gly—Lys—Pro—Val—NH$_2$

This hormone is secreted by the pars intermedia of the pituitary gland and stimulates adenylate cyclase activity, tyrosinase activity, and subsequent melanin production [see Hadley, M. E., C. B. Howard, V. J. Hruby, T. K. Sawyer, and Y. C. S. Young, Pigment Cell 6:323(1980)].

In humans, alpha-MSH is apparently found only in the pituitary gland of the fetus and not in the adult. In adult humans, a certain level of melanin production is genetically determined and constitutively present. Variable melanin synthesis above and beyond this baseline level is directly dependent on UV stimulation, e.g. sunlight; exposure to high levels of sun triggers increased production of melanin, with concomitant darkening of the skin. This response may be an evolutionary adaptation to protect the person against the aging and mutagenic properties of UV. Exposure to low levels of UV results in lower levels of integumental melanin synthesis, fading of skin color, and a diminished blocking effect allowing the skin to absorb greater amounts of radiation. Although adults do not synthesize alpha-MSH in the pituitary gland, human melanocytes will respond to this hormone (and a racemized preparation thereof).

Hypopigmentation of the skin in humans results from local defects in melanin production within the melanocytes, however, the etiology for many such hypopigmentary disturbances is still unknown.

It is estimated that approximately 1% of the world's population is afflicted with some form of hypopigmentation dysfunctions. Although it is known that alpha-MSH and certain analogs of alpha-MSH can cause darkening in amphibians when administered subcutaneously, and that alpha-MSH is associated with skin darkening in adrenalectomized humans when administered intramuscularly [Lerner, A. B., and J. S. McGuire, N. E. J. Med. 270:539–546(1964)], these routes of administration are not suitable for repeated application necessary to achieve and maintain the desired effect. Prior to the present invention no adequate means of treating these hypopigmentation disorders were known.

It has now been discovered that alpha-MSH and certain analogs of alpha-MSH can effectively be administered transcutaneously, and these compounds will reach the melanocytes in active form to stimulate the production of melanin. Thus, according to the present invention, it is now possible and convenient to apply topical compositions comprising alpha-MSH analogs to achieve normalization of hypopigmentation dysfunctions such as postinflammatory hypopigmentation, including pityriasis alba, tinea versicolor, vitiligo, idiopathic guttate hypomelanosis; and nevus depigmentosus. Furthermore, it is now possible to achieve darkening of grey hair due to aging by topical application of alpha-MSH analogs. It is also possible to enhance the value of commercial animal pelts by darkening via topical application of these analogs. In addition, it is now possible to achieve darkening of the skin in the total absence of sun or UV light irradiation.

The present invention's objective is, therefore, to describe a method for the stimulation of melanocyte production in adult humans in the total absence of sun or UV light irradiation, thus providing a safe method of tanning which avoids the need for exposure to the aging and mutagenic effects of high-level US. Not only are the damaging effects of UV previously required to acquire the tan avoided, but once the tan is acquired it should help protect the skin against subsequent exposure to UV irradiation.

Compounds suitable for use in the methods and compositions of the present invention include those disclosed in U.S. Patents 4,457,864 and 4,485,039, the disclosure of which is incorporated in toto herein, alpha-MSH, and compounds of the formula:

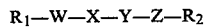

$$R_1—W—X—Y—Z—R_2$$

wherein $R_1$ is selected from the group consisting of Ac—Gly—, Ac—Met—Glu, Ac—Nle—Glu, and Ac—Tyr—Glu—;

W is selected from the group consisting of —His—and —D—His—;

X is selected from the group consisting of —Phe—, —D—Phe—, —Tyr—, —D—Tyr—, —(pNO$_2$)-D—Phe$^7$—;

Y is selected from the group consisting of —Arg—and —D—Arg—;

Z is selected from the group consisting of —Trp— and —D—Trp—; and

R$_2$ is selected from the group consisting of —NH$_2$; —Gly—NH$_2$; and —Gly—Lys—NH$_2$.

As used hereinabove and below, Ala=alanine, Arg=arginine, Glu=glutamic acid, Gly=glycine, His=histidine, Lys=lysine, Met=methionine, Nle=norleucine, Phe=phenylalanine, (pNO$_2$)Phe=paranitrophenylamine, Plg=phenylglycine, Pro=proline, Ser=serine, Trp=tryptophan, TrpFor=N$^i$-formyltryptophane, Tyr=tyrosine, Val=valine. All peptides are written with the acyl-terminal end at the left and the amino terminal end to the right; the prefix "D" before an amino acid designates the D-isomer configuration, and unless specifically designated otherwise, all amino acids are in the L-isomer configuration.

Compounds suitable for use in the present in invention include:

alpha-MSH
[D—Phe$^7$]—alpha-MSH
[Nle$^4$, D—Phe$^7$]—alpha-MSH
[D—Ser$^1$, D—Phe$^7$]—alpha-MSH
[D—Tyr$^2$, D—Phe$^7$]—alpha-MSH
[D—Ser$^3$, D—Phe$^7$]—alpha-MSH
[D—Met$^4$, D—Phe$^7$]—alpha-MSH
[D—Glu$^5$, D—Phe$^7$]—alpha-MSH
[D—His$^6$, D—Phe$^7$]—alpha-MSH
[D—Phe$^7$, D—Arg$^8$]—alpha-MSH
[D—Phe$^7$, D—Trp$^9$]—alpha-MSH
[D—Phe$^7$, D—Lys11]—alpha-MSH
[D—Phe$^7$, D—Pro12]—alpha-MSH
[D—Phe$^7$, D—Val13]—alpha-MSH
[D—Ser$^1$, Nle$^4$, D—Phe$^7$]—alpha-MSH
[D—Tyr$^2$, Nle$^4$, D—Phe$^7$]—alpha-MSH
[D—Ser$^3$, Nle$^4$, D—Phe$^7$]—alpha-MSH
[Nle$^4$, D—Glu$^5$, D—Phe$^7$]—alpha-MSH
[Nle$^4$, D—His$^6$, D—Phe$^7$]—alpha-MSH
[Nle$^4$, D—Phe$^7$, D—Arg$^8$]—alpha-MSH
[Nle$^4$, D—Phe$^7$, D—Trp$^9$]—alpha-MSH
[Nle$^4$, D—Phe$^7$, D—Lys$^{11}$]—alpha-MSH
[Nle$^4$, D—Phe$^7$, D—Pro$^{12}$]—alpha-MSH
[Nle$^4$, D—Phe$^7$, D—Val$^{13}$]—alpha-MSH
[Cys$^4$, Cys$^{10}$]—alpha-MSH
[Cys$^4$, D—Phe$^7$, Cys$^{10}$]—alpha-MSH
[Cys$^4$, Cys$^{11}$]—alpha-MSH
[Cys$^5$, Cys$^{10}$]—alpha-MSH
[Cys$^5$, Cys$^{11}$]—alpha-MSH
[Cys$^4$, Cys$^{10}$]—alpha-MSH
[Cys$^4$, Cys$^{10}$]—alpha-MSH
[Nle$^4$, D—Phe$^7$]—alpha-MSH$_{4-10}$
[Nle$^4$, D—Phe$^7$]—alpha-MSH$_{4-11}$
[D—Phe$^7$]—alpha-MSH$_{5-11}$
[Nle$^4$, D—Tyr$^7$—alpha-MSH$_{4-11}$
[(pNO$_2$)D—Phe$^7$]—alpha-MSH$_{4-11}$
[Tyr$^4$, D—Phe$^7$]—alpha-MSH$_{4-10}$
[Tyr$^4$, D—Phe$^7$]—alpha-MSH$_{4-11}$
[Nle$^4$]—alpha-MSH$_{4-11}$
[Nle$^4$, (pNO$_2$)D—Phe$^7$]—alpha-MSH$_{4-11}$
[Nle$^4$, D—His$^6$, D—Phe$^7$]—alpha-MSH$_{4-11}$
[Nle$^4$, D—Arg$^8$]—alpha-MSH$_{4-11}$
[Nle$^4$, D—Trp$^9$]—alpha-MSH$_{4-11}$
[Nle$^4$, D—Phe$^7$, D—Trp$^9$]—alpha-MSH$_{4-11}$
[Nle$^4$, D—Phe$^7$]—alpha-MSH$_{4-9}$
[Nle$^4$, D—Phe$^7$, D—Trp$^9$]—alpha-MSH$_{4-9}$ Preferred compounds include:
[Nle$^4$, D—Phe$^7$]—alpha-MSH
[Nle$^4$, D—Phe$^7$]—alpha-MSH$_{4-10}$
[Nle$^4$, D—Phe$^7$]—alpha-MSH$_{4-11}$
[Nle$^4$, D—Phe$^7$, D—Trp$^9$]—alpha-MSH$_{4-11}$
[Nle$^4$, D—Phe$^7$]—alpha-MSH$_{4-9}$ These compounds may be synthesized according to procedures shown in U.S. Pat. Nos. 4,457,864 and 4,485,039 or according to well-known methods used in preparing synthetic alpha-MSH. These compounds are superior to alpha-MSH in one or more of the following characteristics: potency as measured by the in vivo and in vitro frog and/or lizard assay; duration of in vivo effect in such assays; and/or resistance to degradation by blood serum enzymes.

The compounds useful in this invention may be administered transdermally, and are formulated in suitable compositions determined by the intended means of administration, according to methods and procedures well-known to those skilled in the art. For example, the compounds suitable for use in this invention may be formulated or compounded with various conventional bases into preparations such as creams, ointments, gels, lotions, or sprays depending upon the desired mode of application of the ingredients of the skin of an individual. In manufacturing these preparations, the composition may also be mixed with conventional thickening agents, emollients, surfactants, pigments, perfumes, preservatives, fillers, and emulsifiers, all of which are well known and conventionally used in the formulation of dermal preparations. Typically, these nonactive ingredients will make up the greater part of the final preparation. Preferably, the compositions are constructed to allow slow-release or timed-release delivery.

A further understanding of the invention can be had from the following non-limiting examples in which all temperature and temperature ranges refer to the centigrade system and the terms ambient or room temperature refer to about 20° C. The term percent or (%) refers to weight percent and the terms mole and moles refer to gram moles.

EXAMPLE 1

Preparation of Compounds

All compounds shown in Examples 1-3 were synthesized by solid-phase synthesis and purified according to the method described in Sawyer et al., P.N.A.S. 77:5754–5758(1980), or Sawyer et al., P.N.A.S. U.S.A. 79:1751–1755(1982), or Sawyer et al., J. Med. Chem. 25:1022–1027(1982).

Briefly summarized, each compound was synthesized by first preparing a p-methylbenzhydrylamine resin to which the desired amino acids was coupled successively as its N$^{alpha}$-Boc derivative. The reactive chain side group of each trifunctional amino acid was protected by incorporation of an appropriate protective group. After all the amino acid residues were coupled to the resin, the amino terminus of the peptide-resin was acetylated. Subsequent to acetylation the protected peptide was cleaved from the resin, and all protecting groups were removed. For cyclic disulfide compounds, the sulfhydryl form was oxidized to the cyclic disulfide compound by ferricyanide oxidation. The crude compound was purified by ion-exchange chromatography on silica gel using appropriate solvents. Optical rotation values were measured at the mercury-green line (646 nm) in a Perkin-Elmer 241 MC Polarimeter.

Alpha-MSH utilized for comparative purposes in Examples 1-3 were prepared as described in Yang et al., Int. J. Pept. Protein Res. 15:130-138(1980). [Nle$^4$]-alpha-MSH, also used for comparative analysis, was either purchased from Penninsula Laboratories (San Carlos, CA) or was prepared as described in Hruby et al., J. Med. Chem. 23:1432(1980).

EXAMPLE 2

Biological effect on in vivo and in vitro melanosome dispersion was examined using the frog (*Rana pipiens*) and the lizard (*Anolis caroliniensis*). [See Hadley et al., Science 213:1025-1027(1981)]; similar examinations were conducted with respect to the duration of its ability to stimulate melanosome dispersion in vitro using the skin bioassay as described in Shimume, Endrochrinology, 54:553-560(1954). The in vitro results are depicted in Table I.

therapeutic and basic research schemes. In the area of diagnostic procedures, it is apparent that compounds of the invention, especially those which have been radioiodinated or coupled with gamma radiation emitters, are exceptionally well suited for use in locating and/or differentially characterizing melanoma cells on the basis of association with melanotropin receptors in such cells. The serum stability of compounds of the invention makes them prime candidates in proposed selective drug delivery systems wherein target tissues are known to have high concentrations and prolonged activity of compounds of the invention in color change-associated phenomena is expected to be duplicated in the context of other biological effects previously noted for naturally occurring melanocyte stimulating hormone and its synthetic analogues.

TABLE I

| POTENCIES AND PROLONGATION OF ALPHA-MSH ANALOGUES | | | | |
|---|---|---|---|---|
| Compound | I | II | III | IV |
| alpha-MSH | 1.0 | 1.0 | — | — |
| Ac—[Nle$^4$]-alpha-MSH$_{4-11}$—NH$_2$ | 0.0019 | 1.54 | +++ | — |
| Ac—[Nle$^4$—D-Phe$^7$]—alpha-MSH$_{4-11}$—NH$_2$ | 0.71 | 8.0 | +++ | +++ |
| Ac—[Nle$^4$—Plg$^7$]—alpha-MSH$_{4-11}$—NH$_2$ | 0.14 | 0.14 | | |
| Ac—[Nle$^4$—D-Plg$^7$]—alpha-MSH$_{4-11}$—NH$_2$ | 0.00030 | 0.00050 | | |
| Ac—[Nle$^4$—Gly$^7$]—alpha-MSH$_{4-11}$—NH$_2$ | 0.005 | 0.00050 | | |
| Ac—[Nle$^4$—Ala$^7$]—alpha-MSH$_{4-11}$—NH$_2$ | 0.02 | 0.009 | | |
| Ac—[Nle$^4$—D-Ala$^7$]—alpha-MSH$_{4-11}$—NH$_2$ | 0.000080 | 0.020 | | |
| Ac—[Nle$^4$—Tyr$^7$]—alpha-MSH$_{4-11}$—NH$_2$ | 0.010 | 0.0090 | | |
| Ac—[Nle$^4$—D-Tyr$^7$]—alpha-MSH$_{4-11}$—NH$_2$ | 0.0020 | 1.0 | | |
| Ac—[Nle$^4$—pNO$_2$Phe$^7$]—alpha-MSH$_{4-11}$—NH$_2$ | 0.0009 | 0.20 | | |
| Ac—[D-Phe$^7$]—alpha-MSH$_{5-11}$—NH$_2$ | 0.01 | | — | |
| Ac—[Nle$^4$—Tyr$^7$]—alpha-MSH$_{4-11}$—NH$_2$ | 0.0002 | | — | |
| Ac—[Nle$^4$—D-Tyr$^7$]—alpha-MSH$_{4-11}$—NH$_2$ | 0.0033 | | + | |
| Ac—[Phe(pNO$_2$)$^7$]—alpha-MSH$_{4-11}$—NH$_2$ | 0.0003 | | | |
| Ac—[D-Phe(pNO$_2$)$^7$]—alpha-MSH$_{4-11}$—NH$_2$ | | | + | |
| Ac—[Ala$^7$]—alpha-MSH$_{4-11}$—NH$_2$ | | | — | |
| Ac—[D-Ala$^7$]—alpha-MSH$_{4-11}$—NH$_2$ | 0.001 | | ± | |
| Ac—[Phe—Gly$^7$]—alpha-MSH$_{4-11}$—NH$_2$ | 0.10 | | — | |
| Ac—[Tyr$^4$—D-Phe$^7$]—alpha-MSH$_{4-10}$—NH$_2$ | 0.005 | | + | |
| Ac—[Tyr$^4$—D-Phe$^7$]—alpha-MSH$_{4-11}$—NH$_2$ | 0.01 | | + | |
| Ac—[Nle$^4$—D-pNO$_2$Phe$^7$]—alpha-MSH$_{4-11}$—NH$_2$ | 0.10 | 4.0 | | |
| Ac—[Nle$^4$—D-His$^6$]—alpha-MSH$_{4-11}$—NH$_2$ | 0.0014 | 0.002 | + | ++ |
| Ac—[Nle$^4$—D-His$^6$—D-Phe$^7$]—alpha-MSH$_{4-11}$—NH$_2$ | 0.0006 | 0.053 | +++ | +++ |
| Ac—[Nle$^4$—D-Arg$^8$]—alpha-MSH$_{4-11}$—NH$_2$ | 0.000016 | 0.0022 | + | + |
| Ac—[Nle$^4$—D-Phe$^7$—D-Arg$^8$]—alpha-MSH$_{4-11}$—NH$_2$ | 0.00010 | 0.0022 | + | +++ |
| Ac—[Nle$^4$—D-Trp$^9$]—alpha-MSH$_{4-11}$—NH$_2$ | 0.61 | 1.7 | + | — |
| Ac—[Nle$^4$—D-Phe$^7$—D-Trp$^9$]—alpha-MSH$_{4-11}$—NH$_2$ | 3.17 | 10.5 | +++ | +++ |
| Ac—[Nle$^4$—D-Phe$^7$—TrpFor$^9$]—alpha-MSH$_{4-11}$—NH$_2$ | 0.033 | | | |
| Ac—[Nle$^4$—D-Phe$^7$—Phe$^9$]—alpha-MSH$_{4-11}$—NH$_2$ | 0.017 | | | |
| Ac—[Nle$^4$—D-Phe$^7$]—alpha-MSH$_{4-11}$—NH$_2$ | 0.012 | | | |
| Ac—[Nle$^4$]-alpha-MSH$_{4-9}$—NH$_2$ | 0.0007 | 0.18 | — | — |
| Ac—[Nle$^4$—D-Phe$^7$]—alpha-MSH$_{4-9}$—NH$_2$ | | 7.14 | | ++ |
| Ac—[Nle$^4$—D-Phe$^7$—D-Trp$^9$]—alpha-MSH$_{4-9}$—NH$_2$ | 0.03 | 3.8 | + | + |
| Ac—[Nle$^4$—D-Phe$^7$]—alpha-MSH$_{4-10}$—NH$_2$ | 0.02 | | ± | |
| Ac—[Nle$^4$—D-Phe$^7$]—alpha-MSH$_{4-11}$—NH$_2$ | 0.16 | | + | |

I = Relative Potency Frog
II = Relative Potency Lizard
III = Prolonged Frog
IV = Prolonged Lizard Resistance to serum proteolytic enzyme degradation of the compounds according to the present invention were demonstrated by incubating the compounds at 37° C. under sterile conditions in Corning flasks containing Ham's F-10 media containing 10% horse serum and 2% fetal calf serum. In this procedure, samples of the media containing the peptides (10 nM) were removed at time zero and at 24, 48, and 72 hours. The samples were immediately frozen, and assays for biological activity using the in vitro frog skin bioassay. Using this protocol, resistance to serum proteolytic enzyme degradation was clearly demonstrated.

The remarkable properties of compounds of the invention also render them useful as substitutes for alpha-MSH and [Nle$^4$]-alpha-MSH in existing diagnostic, Examples 3 and 4 demonstrate the relative effects of topical or subcutaneous alpha-MSH, [Nle$^4$, D—Phe$^7$]—alpha-MSH, [Nle$^4$, D—Phe$^7$]—alpha-MSH$^{4-10}$, and [Nle$^4$, D—Phe$^7$]—alpha-MSH$^{4-11}$ on follicular melanogenesis in the mouse.

EXAMPLE 3

Subcutaneous Injection

Alpha-MSH and [Nle$^4$, D-Phe$^7$]—alpha-MSH were synthesized. Mice (C57BL/6JA$^y$) originally obtained from the Jackson Laboratories (Bar Harbor, ME) were raised in our laboratory with continuous access to food and water.

Alpha-MSH has been shown to stimulate follicular melanogenesis in the C57BL/6JA$^y$ yellow mouse both in vivo and in vitro. We found that alpha-MSH required a ten-thousand fold higher concentration compared to the analogue, [Nle$^4$, D-Phe$^7$]—alpha-MSH, when injected into the mouse to stimulate melanogenesis. A single injection (0.05 ml) of the analogue ($10^{-6}$M) resulted in a shift from phaeomelanin production to eumelanin synthesis within hair bulbs 24 hours later, and eumelanogenesis continued for 96 hours after the one injection. The animal's entire coat color was found to be changed by 14 consecutive daily injections of [Nle$^4$, D-Phe$^7$]—alpha-MSH. Melanotropins induce melanogenesis only during hair growth, and melanosomes are continuously incorporated into cells of the hair shaft as long as the hair remains in the anagen (proliferative) phase of the hair cycle. Eumelanin synthesis in only those hairs currently growing results in the formation of a pattern showing the specific areas on the animal in the anagen phase at the time of hormone injection.

EXAMPLE 4

Topical Application

Alpha-MSH and [Nle$^4$, D-Phe$^7$]-alpha-MSH were each dissolved in a vehicle consisting of polyethylene glycol (26% PEG 400 and 74% PEG 3350, by weight) and applied topically to the skin. An area (2-3 cm$^2$) of hair on the posterior dorsum of 48-day old mice was plucked; in mice of this age, hair follicles in the posterior dorsum are in the telogen (resting) phase of the hair cycle. Plucking hairs from resting follicles stimulates new hair growth and by 7 days later those hairs being erupting through the skin surface. Mice were fitted with cardboard collars to prevent investigation and spread of the ointment to non-treated areas of the skin and then housed individually in cages. The ointment containing [Nle$^4$, D-Phe$^7$-]alpha-MSH (0.5 ml, $10^{-6}$M) was applied daily to the plucked area at the time of new hair eruption. A sample of emerging hair was removed prior to topical application of the melanotropin and every 24 hours thereafter for seven days.

Microscopic examination revealed eumelanin within hair bulbs by 24 hours following application of the analogue. Continued daily application of the analogue resulted in continuous eumelanin synthesis and transfer of melanosomes to cells moving into the hair the hair bulbs of the treated site but was observed microscopically in hair bulbs taken from untreated areas of the animal where hair growth was in progress. Eumelanin was not visible within hairs taken from control mice. Electron microscopic examination confirmed the presence of eumelanotic melanosomes within follicular melanocytes of mice treated with [Nle$^4$, D-Phe$^7$]-alpha-MSH. Only phaeomelanosomes were present in mice treated with the control ointment containing no melanotropin. Alpha-MSH, at the same concentrations as the analogue ($10^{-8}$ M or lower) failed to induce eumelanogenesis even when applied to the skin of mice for as long as 14 days. Alpha-MSH applied at a higher concentration ($10^{-5}$ to $10^{-7}$ M) did result in both local and systemic follicular melanogenesis.

These examples demonstrate the transdermal delivery of both the native hormone, alpha-MSH, and the analogue, [Nle$^4$, D-Phe$^7$]-alpha-MSH. The effectiveness of the analogue may relate to the fact that the peptide is about 10 to 1000 times more potent than alpha-MSH as determined in several bioassays. In addition, the analogue is resistant to enzymatic inactivation, unlike alpha-MSH which is rapidly inactivated. Both male and female mice responded similarly to the melanotropins. Transdermal delivery of the analogue occurred equally well when applied to a shaved area of the skin or when applied to the base of the hairs. These results demonstrate that transport of the melanotropins proceeded through intact areas of the skin. Although follicular melanogensis could be noted by 24 hours post-application of [Nle$^4$, D—Phe$^7$]-alpha-MSH, transdermal delivery of the peptide to melanocytes was probably much more rapid since activation of tyrosinase activity is a genomic event that involves both transcriptional and translational processes that are known to occur only after many hours of contact with a melanotropin.

EXAMPLE 5

Example 4 was repeated with compositions comprising alpha-MSH or [Nle$^4$, D—Phe$^7$]-alpha-MSH in propylene glycol and 1-dodecylazacycloheptan-2-one [a synthetic polar surfactant previously known to enhance transdermal penetration of other compounds. See, e.g., Stoughton, R. B., Arch. Dematol. 118:479(1982); Stoughton, R. B. and W. O. McClure, Drug Devel. Indust. Pharm. 9(4):725(1983); (Azone)]. Although the vehicle was a solid at room temperature, it immediately softened and spread easily when applied to the shaved skin of the mouse.

In this example, the azone concentration was 1.8% and the MSH final concentration was either 0.001% (1mg/100g cream base) or 0.003%.

EXAMPLE 6

Mice

Mice with some pigmentation on their skin were treated with the same cream as Example 5. The treated area remained unchanged; however, the tail turned significantly darker.

The tails of the treated animals darkened in spite of not being directly treated topically. Histologic examination revealed increased pigment in the areas of non-follicular melancytes. These results lead to the conclusion that (1) [Nle 4, D—Phe 7]-alpha-MSH has systemic effects after topical application, and (2) non-follicular melanocytes are sensitive to the melanogenic effects of these melanotropins.

EXAMPLE 7

The Ames microbacterial assay was used for these tests which were performed both with and without a microsomal enzyme/NADPH generating system. Briefly, this test measures the number of reverse mutations which occur in special histidine-dependent strains of Salmonella typhimurium. Positives (mutations) are scored as the number of revertant cells which are able to form colonies in a histidine-deficient growth medium after exposure to a mutagenic substance.

The specific tests involved three melanotropins: alpha MSH, [Nle$^4$—D—Phe$^7$]alpha MSH, and [Ac=[-Nle$^4$, D-Phe$^7$]-alpha—MSH$_{4\text{-}10}$-NH$_2$. All substances were dissolved in sterile 0.9% sodium chloride (without preservatives) to concentrations of $10^{-2}$, $10^{-3}$ and $10^{-4}$ Molar. The TA-98 strain of S. typhimurium was used and experiments were performed with and without exposure to S-9 rat liver microsomal enzymes and an NADPH generating system. This enzyme cocktail can metabolically activate some compounds to mutagenic species. In addition to the melanotropins, Doxorubicin (Adriamycin TM) was also simultaneously tested. Doxorubicin is a DNA-intercalating antibiotic which is known to be highly mutagenic in this assay. It was thus included to act as a positive control. The following table shows the results of these tests. For the actual evaluation of revertants, the identity of the specific test compound was blinded.

| COMPOUND (CONC.) | | REVERTANTS PER PLATE* | |
|---|---|---|---|
| | | WITHOUT S-9 | WITH S-9 |
| Adriamycin | 1.0 g/ml | 0 | 100 |
| | 10 g/ml | 230 | 2500 |
| | 100 g/ml | 1940 | 2930 |
| Alpha MSH | $10^{-2}$ M | 0 | 0 |
| | $10^{-3}$ M | 0 | 0 |
| | $10^{-4}$ M | 0 | 0 |
| [Nle$^4$, D-Phe$^7$]- | $10^{-2}$ M | 0 | 0 |
| alpha MSH | $10^{-3}$ M | | |
| | $10^{-4}$ M | | |
| AC—[Nle$^4$, D-Phe$^7$] | | | |
| Alpha MSH$_{9-10}$—NH$_{22}$ | $10^{-2}$ M | 0 | 0 |
| | $10^{-3}$ M | 0 | 0 |
| | $10^{-4}$ M | 0 | 0 |

*Experimental counts are normally adjusted by subtraction of spontaneous revertants/plate (56 in this run).

These preliminary results suggest none of the natural or synthetic melanotropins are mutagenic in vitro. Adriamycin was significantly mutagenic and this increased after exposure to S-9 microsomal enzyme.

Thus, the bacterial assay and the metabolic activating system appeared to be working well and the lack of mutagenicity with the melanotropins does not appear to be artifact.

EXAMPLE 8

Toxicology

Six rats were injected with [Nle$^4$, D—Phe$^7$]-alpha-MSH (0.2 ml of $10^{-4}$M solution of the peptide; 0.02 mg daily for 5 consecutive days). The four female and two male rats were apparently no worse for the treatment. On the last day of the treatment the animals were sacrificed and serum samples obtained. Blood glucose analysis revealed that glucose levels between control and experimental animals did not differ. If the melanotropins were to stimulate the adrenal then it might be expected that blood glucose levels would be altered (as in Cushing's disease in humans).

Mice injected with the melanotropin at the same abnormally high concentrations of the hormone were apparently not affected. Even their behavior did not seem to change during the times of observation.

Additionally studies were performed in male CD-2 injected introperitoneally with 0.25 ml of 20-$^3$M of [Nle$^4$, D—Phe$^7$]MSH. Core temperatures were monitored by rectal probes connected to a digital thermal transducer. There were not consistent changes in the core temperatures which averaged 35.2° C. for up to 24 hours post-injection. The activity level was also normal in these animals. Twenty four hours after dosing, the mice were sacrificed by rapid cervical dislocation and blood removed for analysis of hepatic and renal chemistries, and for characterization of hematologic indices. These studies showed no alterations in liver or kidney function. Serum levels of electrolytes were normal. The serum cortisol levels were also normal. Analyses of whole blood showed no hematologic toxicities and there were normal levels of white blood cells, red blood cells and platelets. The red blood cell characteristics (size, hemoglobin level) were normal. There was not significant weight change in any of the animals in this short-term study.

EXAMPLE 9

Human Cadaver and Excised Skin Models for Transdermal

Delivery or Melanotropins

Human cadaver and excised skin from mastectomies, face lifts, etc. has been used to determine the in vitro penetration of alpha-MSH analog [Nle$^4$H,D—PheY7H]-alpha-MSH. Studies have shown that in vitro transdermal delivery in these types of skin accurately predicts the in vitro situation.

Subcutaneous tissue is removed from these skin samples and they are set up on a specially designed penetration cell [LGA]at 38° C. for 24 hours. AlphaMSH analog in PEG is applied to the epidermal surface. Saline bathes the dermal surface of the sample. The amount of alpha-MSH analog traversing the skin into the saline is quantitated by frog skin bioassay.

Data from these experiments supports the conclusion that:

(1) Mouse skin is well penetrated by the analog, correlating with in vivo studies;
(2) Full thickness intact abdominal thoracic human skin (epidermis+ dermis) is not penetrated entirely. This is an important finding for topical application (i.e. the drug may stay localized in the skin).
(3) Human scalp full thickness skin is penetrated by the analog (possibly associated with the presence of numerous hair follicles).
(4) Split skin samples of human epidermis (0.5 mm and 0.7 mm) are penetrated by the analog suggesting that the stratum corneum is not the main barrier to the analog, which should therefore be able to reach the melanocytes in the epidermis.

Thus, while we have illustrated and described the preferred embodiments of our invention, it is to be understood that this invention is capable of variation and modification, and we therefore do not wish to be limited to the precise terms set forth, but desire to avail ourselves of such changes and alterations which may be made for adapting the invention to various usages and conditions. Accordingly, such changes and alterations are properly intended to be within the full range of equivalents, and therefore within the purview, of the following claims.

Having thus described our invention and the manner and process of making and using it, in such full, clear, concise, and exact terms so as to enable any person skilled in the art to which it pertains, or with which it is most nearly connected, and to make and use the same:

We claim:

1. A method of stimulating melanin production in a vertebrate which comprises administering to said vertebrate in an amount sufficient to cause stimulation of melanocytes a compound of the group:
   (1) alpha-MSH having the amino acid formula:
   Ac—Ser—Tyr—Ser—Met—Glu—His—Phe—Arg—Trp—Gly—Lys—Pro—Val—NH$_2$;
   (2) Alpha-MSH analogues having the formula:
   Ac—Ser—Tyr—Ser—M—Glu—His—D—Phe—Arg—Trp—Gly—Lys—ProVal—NH$_2$ wherein M is selected from the group consisting of Met, Nle, and Cys;

(3) analogues of alpha-MSH having the formula:
$R_1-W-X-Y-Z-R_2$
wherein $R_1$ is selected from the group consisting of Ac—Gly, Ac—Met—Glu, Ac—Nle—Glu and Ac—Tyr—Glu;
wherein W is selected from the group consisting of His, and D—His;
wherein X is selected from the group consisting of Phe, D—Phe, Tyr, D—Tyr, and (pNO$_2$)-D—Phe;
wherein Y is selected from the group consisting of Arg and D—Arg;
wherein Z is selected from the group consisting of Trp and D—Trp; and
wherein $R_2$ is selected from the group consisting of NH$_2$, Gly—NH$_2$, and Gly—Lys—NH$_2$; and (4) alpha-MSH analogues selected from the group consisting of
[Nle$^4$, D—Phe$^7$]—alpha—MSH
[Nle$^4$, D—Phe$^7$]—alpha—MSH$_{4-10}$
[Nle$^4$, D—Phe$^7$]—alpha MSH$_{4-11}$
[Nle$^4$, D—Phe$^7$, D—Trp$^9$]—alpha—MSH$_{4-11}$
[Nle$^4$, D—Phe$^7$]—alpha—MSH$_{4-9}$ 2. The method of claim 1 wherein the compound is [Nle$^4$, D—Phe$^7$]—alpha—MSH.

3. The method of claim 1 wherein the compound is [Nle$^4$, D—Phe$^7$]—alpha—MSH$_{4-10}$.

4. The method of claim 1 wherein the compound is [Nle$^4$, D—Phe$^7$]—alpha—MSH$_{4-11}$.

5. The method of claim 1 wherein the compound is [Nle$^4$, D—Phe$^7$, D—Trp$^9$]—alpha—MSH$_{4-11}$.

6. The method of claim 1 wherein the compound is [Nle$^4$, D—Phe$^7$]—alpha—MSH$_{4-9}$.

7. The method of claim 1 wherein the compound is Ac—Ser—Tyr—Ser—Met—Glu—His—Phe—Arg—Trp—Gly—Lys—Pro—Val—NH$_2$;

8. The method of claim 1 wherein the compound is Ac—Ser—Tyr—Ser—Cys—Glu—His—D—Phe—Arg—Trp—Gly—Lys—Pro—Val—NH$_2$ 9. A method of claim 1 wherein the compound is an analogue of alpha-MSH in which X is D-Phe.

10. A method of claim 1 wherein the compound is an analogue of alpha-MSH in which $R_1$ is Ac—Nle—Glu.

11. A method of claim 1 wherein the compound is an analogue of alpha-MSH is which $R_1$ is Ac—Nle—Glue, and X is D—Phe.

12. A method for the stimulation of integumental melanocytes in a vertebrate which comprises administrating topically to the epidermal tissue of said vertebrate in an amount sufficient to cause stimulation, a compound of the group:

(1) alpha-MSH having the amino acid formula:
Ac—Ser—Tyr—Ser—Met—Glu—His—Phe—Arg—Trp—Gly—Lys—Pro—Val—NH$_2$;

(2) alpha—MSH analogues having the formula:
Ac—Ser—Tyr—Ser—M—Glu—His—D—Phe—Arg—Trp—Gly—Lys—Pro—Val—NH$_2$
wherein M is selected from the group consisting of Met, Nle and Cys;

(3) analogues of alpha—MSH having the formula:
$R_1-W-X-Y-Z-R_2$ wherein $R_1$ is selected from the group consisting of Ac—Gly, Ac—Met—Glu, Ac—Nle—Glu, and Ac—Tyr—Glu' wherein W is selected from the group consisting of His and D—His; wherein X is selected from the group consisting of Phe, D—Phe—Tyr, D—Tyr, and (pNO$_2$)D—Phe; wherein Y is selected from the group consisting of Arg and D—Arg; wherein Z is selected from the group consisting of Trp and D—Trp; and wherein $R_2$ is selected from the group consisting of NH$_2$, Gly—N$_2$ and Gly—Lys—NH$_2$; and (4) alpha—MSH analogues selected from the group consisting of
[Nle$^4$, D—Phe$^7$]—alpha—MSH
[Nle$^4$, D—Phe$^7$]—alpha—MSH$_{4-10}$
[Nle$^4$, D—Phe$^7$]—alpha—MSH$_{4-11}$
[Nle$^4$, D—Phe$^7$, D—Trp$^9$[—alpha—MSH$_{4-11}$
[Nle$^4$, D—Phe$^7$]—alpha—MSH$_{4-9}$ 13. The method of claim 12 wherein the compound is [Nle$^4$, D—Phe$^7$]—alpha—MSH$_{4-10}$.

14. The method of claim 12 wherein the compound is [Nle$^4$, D—Phe$^7$]—alpha—MSH$_{4-11}$.

15. The method of claim 12 wherein the compound is [Nle$^4$, D—Phe$^7$, D—Trp$^9$]—alpha—MSH$_{4-11}$.

16. The method of claim 12 wherein the compound is [Nle$^4$, D—Phe$^7$]—alpha—MSH$_{4-9}$.

17. The method of claim 12 wherein the compound is Ac—Ser—Tyr—Ser—Met—Glu—His—Phe—Arg—Trp—Gly—Lys—ProVal—NH$_2$;

18. The method of claim 12 wherein the compound is Ac—Ser—Tyr—Ser—Cys—Glu—His—D—Phe—Arg—Trp—Gly—Lys—ProVal—NH$_2$ 19. A method of claim 12 wherein the compound is an analogue of alpha—MSH in which X is D—Phe.

20. A method of claim 12 wherein the compound is an analogue of alpha—MSH in which $R_1$ is Ac—Nle—Glu.

21. A method of claim 12 wherein the compound is an analogue of alpha—MSH is which $R_1$ is Ac—Nle—Glu, and X is D—Phe.

* * * * *

UNITED STATES PATENT AND TRADEMARK OFFICE
CERTIFICATE OF CORRECTION

PATENT NO. : 4,866,038
DATED : Sept. 12, 1989
INVENTOR(S) : Victor J. Hruby et al.

It is certified that error appears in the above-indentified patent and that said Letters Patent is hereby corrected as shown below:

Column 11, lines 38 and 39, delete "Ar-g", and insert -- Arg --.

Column 11, lines 41 and 42, delete "Ar-g", and insert -- Arg --.

Column 11, line 48, delete "Glue", and insert -- Glu --.

Column 12, line 15, delete "Glu'", and insert -- Glu --.

Column 12, line 23, delete "N$_2$", and insert -- NH$_2$ --.

Column 12, line 29, delete "[-alpha", and insert -- ]-alpha --.

Column 12, lines 40 and 41, delete "Ar-g", and insert -- Arg --.

Column 12, lines 43 and 44, delete "Ar-g", and insert -- Arg --.

Signed and Sealed this

Sixth Day of September, 1994

Attest:

BRUCE LEHMAN

*Attesting Officer*   *Commissioner of Patents and Trademarks*